(12) United States Patent
Adams et al.

(10) Patent No.: US 8,048,062 B2
(45) Date of Patent: Nov. 1, 2011

(54) CATHETER ASSEMBLY AND METHOD FOR INTERNALLY ANCHORING A CATHETER IN A PATIENT

(75) Inventors: Mark L. Adams, Sandy, UT (US); William J. Shaw, Cambridge, MA (US); Donald C. Hovey, Sherborn, MA (US); Luis J. Maseda, Natick, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1495 days.

(21) Appl. No.: 11/323,913

(22) Filed: Dec. 30, 2005

(65) Prior Publication Data

US 2007/0156117 A1    Jul. 5, 2007

(51) Int. Cl.
*A61M 25/16* (2006.01)
(52) U.S. Cl. .................................. 604/535; 604/533
(58) Field of Classification Search ............ 604/96.01, 604/164.01, 523, 533–284
See application file for complete search history.

(56) References Cited

U.S. PATENT DOCUMENTS

| | | |
|---|---|---|
| 3,540,451 A | 11/1970 | Zeman |
| 3,964,470 A | 6/1976 | Trombley |
| 4,004,298 A | 1/1977 | Freed |
| 4,344,435 A | 8/1982 | Aubin |
| 4,668,217 A | 5/1987 | Isono |
| 4,861,334 A | 8/1989 | Nawaz |
| 4,900,306 A | 2/1990 | Quinn et al. |
| 5,112,310 A | 5/1992 | Grobe |
| 5,167,627 A | 12/1992 | Clegg et al. |
| 5,391,159 A | 2/1995 | Hirsch et al. |
| 6,030,364 A | 2/2000 | Durgin et al. |
| 6,319,231 B1 * | 11/2001 | Andrulitis .................. 604/175 |
| 6,402,722 B1 | 6/2002 | Snow et al. |
| 2004/0059293 A1 | 3/2004 | Chu et al. |

FOREIGN PATENT DOCUMENTS

WO    WO 02/13901 A2    2/2002

* cited by examiner

*Primary Examiner* — Kevin C Sirmons
*Assistant Examiner* — Phillip Gray
(74) *Attorney, Agent, or Firm* — Kenyon & Kenyon LLP

(57) ABSTRACT

A catheter assembly and method for internally anchoring a catheter in a patient. According to one embodiment, the catheter assembly includes a catheter, a tubular fitting coupled to one end of the catheter, and an internal bolster coaxially mounted around the tubular fitting. The tubular fitting has a waist portion, and the internal bolster is secured thereto by a snap-fit. To internally anchor the catheter in a patient, one inserts the end of the catheter to which the fitting is coupled into the patient and then, while the fitting and its coupled end of the catheter are within the patient, inserts the internal bolster over the fitting until it snap-fits into place over the waist portion, thereby internally anchoring the catheter within the patient.

31 Claims, 11 Drawing Sheets

CATHETER ASSEMBLY AND METHOD FOR INTERNALLY ANCHORING A CATHETER IN A PATIENT

BACKGROUND OF THE INVENTION

The present invention relates generally to medical catheters and relates more particularly to medical catheters of the type having an internal bolster disposed at one end of said medical catheter for retaining said end of said medical catheter within a patient.

Certain patients are unable to take food and/or medications transorally due to an inability to swallow. Such an inability to swallow may be due to a variety of reasons, such as esophageal cancer, neurological impairment and the like. Although the intravenous administration of food and/or medications to such patients may be a viable short-term approach, it is not well-suited for the long-term. Accordingly, the most common approach to the long-term feeding of such patients involves gastrostomy, i.e., the creation of a feeding tract or stoma between the stomach and the upper abdominal wall. (A less common approach involves jejunostomy, i.e., the creating of a feeding tract or stoma leading into the patient's jejunum.) Feeding is then typically performed by administering food through a catheter or feeding tube that has been inserted into the feeding tract, with one end of the feeding tube extending into the stomach and being retained therein by an internal anchor or bolster and the other end of the feeding tube extending through the abdominal wall and terminating outside of the patient.

Although gastrostomies were first performed surgically, most gastrostomies are now performed using percutaneous endoscopy and result in the implantation in the patient of a feeding tube/internal bolster assembly (said feeding tube/internal bolster assembly also commonly referred to as a percutaneous endoscopic gastrostomy (PEG) device). Two of the more common percutaneous endoscopic techniques for implanting a PEG device in a patient are "the push method" (also known as "the Sacks-Vine method") and "the pull method" (also known as "the Gauderer-Ponsky method"). Information regarding the foregoing two methods may be found in the following patents, all of which are incorporated herein by reference: U.S. Pat. No. 5,391,159, inventors Hirsch et al., which issued Feb. 21, 1995; U.S. Pat. No. 5,167,627, inventors Clegg et al., which issued Dec. 1, 1992; U.S. Pat. No. 5,112,310, inventor Grobe, which issued May 12, 1992; U.S. Pat. No. 4,900,306, inventors Quinn et al., which issued Feb. 13, 1990; and U.S. Pat. No. 4,861,334, inventor Nawaz, which issued Aug. 29, 1989.

According to the push method, one end of an endoscope is intubated (i.e., inserted) into a patient's mouth and is passed through the esophagus into the stomach. After distension of the stomach by inflation, an entry site on the abdomen is identified using the endoscope for transillumination, and an incision is made by passing the tip of a needle coupled to an outer cannula through the abdominal and stomach walls and into the stomach. One end of the outer cannula remains outside of the body and acts as a stop to limit insertion of the needle and outer cannula into the stomach. A snare is inserted into the stomach via the endoscope and is looped over the inserted end of the needle. The snare is then "walked" up the needle until the outer cannula is snared. The snared cannula is then pulled externally to tack the cannula to the stomach and, in turn, to secure the stomach wall to the abdominal wall. The needle is then removed from the patient while keeping the cannula in place. A first end of a flexible guidewire (also known in the art as a "pushwire") is then passed through the cannula and into the stomach where it is grasped by the snare, the second end of the guidewire remaining external to the patient. The endoscope and the snare are then withdrawn from the mouth of the patient to deliver the first end of the guidewire.

A push-type catheter implanting assembly is then inserted over the first end of the guidewire and is pushed over the guidewire towards its second end. The push-type catheter implanting assembly typically comprises a gastrostomy feeding tube, the gastrostomy feeding tube having a dome-shaped internal bolster disposed at its trailing end and having a tubular dilator serially connected to its leading end. The gastrostomy feeding tube and the internal bolster are typically made of a soft, biocompatible material, like silicone rubber, and typically form a unitary structure. The dilator, which tapers in outer diameter from its trailing end to its leading end, is typically made of polyethylene or a like material which is stiffer than silicone but which still possesses some flexibility. Advancement of the push-type catheter implanting assembly over the guidewire continues until the front end of the dilator reaches the cannula and pushes the cannula out through the abdominal wall of the patient. The front end of the dilator is then pulled through the abdominal wall until the front end of the gastrostomy feeding tube emerges from the abdomen and, thereafter, the internal bolster at the rear end of the gastrostomy feeding tube engages the stomach wall. The guidewire is then removed from the patient. The clinician then re-intubates the patient with the endoscope and uses an optical channel in the endoscope to inspect whether the internal bolster is properly seated in the stomach.

If the internal bolster is properly placed against the stomach wall, a length of the externally-extending portion of the implanted gastrostomy feeding tube is then typically cut and removed from the implanted tube to reduce the externally-extending portion of the tube to a desired length (typically about 4-6 inches). (The removal of the leading end of the gastrostomy feeding tube also results in the removal of the dilator, which is connected thereto.) An external bolster is typically secured to the remaining externally-extending portion of the feeding tube to engage the abdomen in such a way as to prevent longitudinal movement of the feeding tube into the stomach. Additionally, a "Y-port" adapter is typically attached to the external end of the feeding tube, the Y-port adapter being adapted to receive a pair of connector tips through which food and/or medications may be dispensed. In addition, a detachable locking clip is typically secured to the implanted feeding tube at a point between the external bolster and the Y-port adapter to prevent gastric fluids from escaping through the proximal end of the feeding tube when the feeding tube is not in use.

The pull method is similar in some respects to the above-described push method, the pull method differing from the push method in that, after the cannula is snared and the needle is removed therefrom, a looped first end of a suture (also known in the art as a "pullwire") is inserted through the cannula and into the stomach where it is grasped by the snare, the second end of the suture remaining external to the patient. The endoscope and the snare are then withdrawn from the mouth of the patient to deliver the first end of the suture. The first end of the suture is then coupled to the leading end of a pull-type catheter implanting assembly, the pull-type catheter implanting assembly typically comprising a gastrostomy feeding tube having an internal bolster integrally formed at its trailing end and a plastic fitting attached to its leading end. The plastic fitting typically has a barbed rear portion mounted within the leading end of the feeding tube and a conical front portion that serves as a dilator, said conical front portion tapering in diameter from the leading end of the feeding tube to a front tip. A wire loop is fixed to the front tip of the plastic fitting, the first end of the suture being tied to the wire loop. Using the second end of the suture, the pull-type catheter implanting assembly is then pulled retrograde through the patient until the gastrostomy feeding tube emerges from the abdomen of the patient and the internal bolster engages the stomach wall of the patient. Next, as is the case in the push method, the clinician then re-intubates the patient with the endoscope in order to visually inspect the placement of the internal bolster within the stomach. If the bolster is properly seated in the stomach, the externally-extending portion of the implanted gastrostomy feeding tube is then typically cut to a desired length and one or more of an external bolster, a Y-port and a clamp are attached to the feeding tube.

In addition to the above-described endoscopic techniques for implanting PEG devices, there also exist direct percutaneous techniques.

Typically, such direct percutaneous techniques involve (i) inserting an endoscope into the patient and, through transillumination, identifying a desired insertion site; (ii) using sutures or T-fasteners, placed one at a time, to secure the abdominal wall to the stomach wall in a plurality of locations surrounding the future insertion site; (iii) using a scalpel to make an incision at the insertion site; (iv) using a series of dilators to enlarge the insertion site opening until said opening is large enough to pass therethrough the internal bolster at the distal end of a gastrostomy tube; and (v) sliding an external bolster over the proximal end of the gastrostomy tube down to skin level over the T-fastener wires or sutures.

Another type of direct percutaneous technique is disclosed in U.S. Pat. No. 6,030,364, inventors Durgin et al., which issued Feb. 29, 2000, and which is incorporated herein by reference. In this patent, there is disclosed a method and apparatus for the percutaneous placement of gastro-intestinal tubes, the apparatus comprising a longitudinal penetration device; a hollow, tapered dilator; and a sheath having a central lumen extending therethrough. The penetration device is placed within the sheath, pushed distally to penetrate the target organ, and then removed from the sheath. After the penetration device is removed, the dilator is inserted into the central lumen of the sheath until it penetrates the target organ, so that the sheath and the penetration are radially dilated as the dilator passes through the sheath. The sheath is then pulled in the proximal direction to counter-balance the distal insertion force. A gastro-intestinal tube is inserted into the hollow center, and pushed distally until it exits the distal end of the dilator. The dilator and sheath are then removed from the target organ.

Still another type of direct percutaneous technique is disclosed in U.S. Pat. No. 6,402,722, inventors Snow et al., which issued Jun. 11, 2002, and which is incorporated herein by reference. In this patent, there is disclosed an apparatus and method for percutaneously placing gastrostomy tubes. The method enables percutaneous placement through an existing penetration, as well as placement where no penetration exists. The apparatus comprises a gastrostomy tube having an internal bolster which can be manipulated such that it has a reduced lateral extent; an axially-extending hollow sleeve which can surround the bolster to hold it in a position of reduced lateral extent; and a rip-cord capable of tearing the sheath. In a preferred embodiment, the internal bolster is folded to have a smaller diameter, the sleeve is placed over the bolster and shrunk down to a smaller diameter. The rip-cord runs distally along the outside of the tube, between the sleeve and the internal bolster, wraps over the distal end of the sleeve and runs proximally along the length of the tube. The replacement tube can then be pushed through a stoma. Once in place, the rip cord is pulled to tear away the sleeve, thereby allowing the bolster to revert to its original lateral extent.

Still yet another type of direct percutaneous technique is disclosed in U.S. Published Patent Application No. US-2004-0059293-A1, which was published Mar. 25, 2004, and which is incorporated herein by reference.

SUMMARY OF THE INVENTION

It is an object of the present invention to provide a novel catheter assembly.

Therefore, according to one aspect of the present invention, there is provided a catheter assembly comprising (a) a catheter, said catheter having a first end and a second end; (b) a tubular fitting, said tubular fitting being secured to said first end of said catheter; and (c) a bolster, said bolster being mounted around said tubular fitting.

In a first preferred embodiment, the tubular fitting includes an externally threaded portion, and the bolster is an internal bolster that includes an internally threaded opening, the externally threaded portion and the internally threaded opening being screw-fit together. In a second preferred embodiment, the tubular fitting includes a waist portion of decreased outer diameter, and the bolster is an internal bolster having an opening appropriately sized for a snap-fit with the waist portion, the tubular fitting being inserted into the opening and secured thereto by a snap-fit. In a third preferred embodiment, the tubular fitting includes a plurality of external barbs, and the bolster is an internal bolster that includes an opening having a plurality of internal barbs, the external barbs matingly engaged with the internal barbs.

According to another aspect of the invention, there is provided a catheter assembly comprising (a) a catheter, said catheter having a first end and a second end; (b) a bolster removably mounted on said first end of said catheter; and (c) magnetic means for retaining said bolster on said catheter. Preferably, the removably mounted bolster is an internal bolster.

According to yet another aspect of the invention, there is provided a catheter assembly comprising (a) a catheter, said catheter having a first end and a second end; and (b) an internal bolster, said internal bolster being reversibly detachably coupled to said first end of said catheter.

The present invention is also directed at a catheter assembly kit. According to one aspect of the invention, said catheter assembly kit comprises (a) a catheter, said catheter having a first end and a second end; (b) a bolster, said bolster not being physically coupled to said catheter; and (c) means for physically coupling said bolster to said first end of said catheter. Preferably, said bolster is an internal bolster.

The present invention is further directed at a method for internally anchoring a catheter in a patient, said method comprising the steps of (a) providing a catheter, said catheter having a first end and a second end; (b) providing an internal bolster, said internal bolster not being physically coupled to said catheter; (c) then, inserting said first end of said catheter into a patient; and (d) while said first end of said catheter is disposed within the patient, physically coupling said internal bolster to said first end of said catheter so as to internally anchor the catheter within the patient. The foregoing method may be used for initial placement of a PEG device but is not limited to such an application.

For purposes of the present specification and claims, various relational terms like "top," "bottom," "proximal" and "distal" are used to describe the present invention when said invention is positioned in or viewed from a given orientation.

It is to be understood that, by altering the orientation of the invention, certain relational terms may need to be adjusted accordingly.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration certain embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts.

DETAILED DESCRIPTION OF PREFERRED EMBODIMENTS

Figure 1:
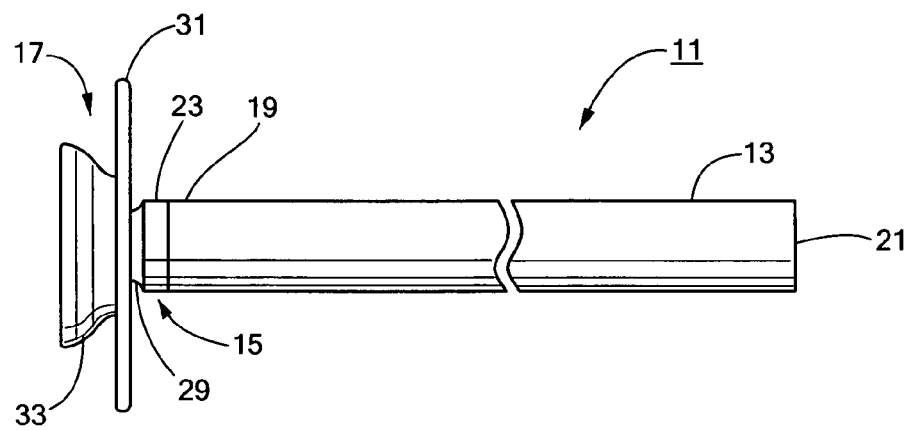
FIG. 1 is a side view of a first embodiment of a catheter assembly constructed according to the teachings of the present invention.
Figure 2:
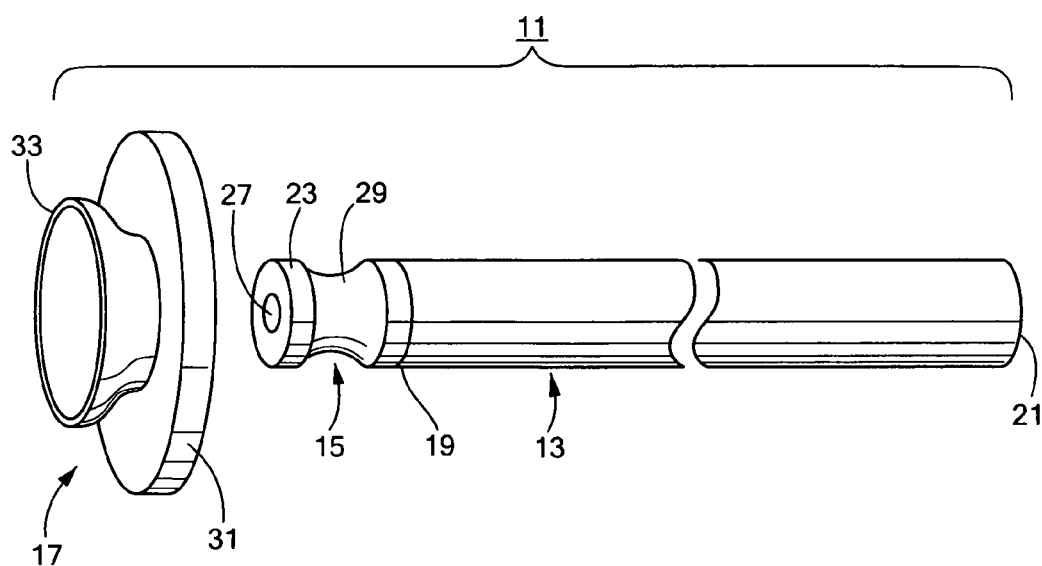
FIG. 2 is a partially exploded perspective view of the catheter assembly shown in FIG. 1.
Figure 3:
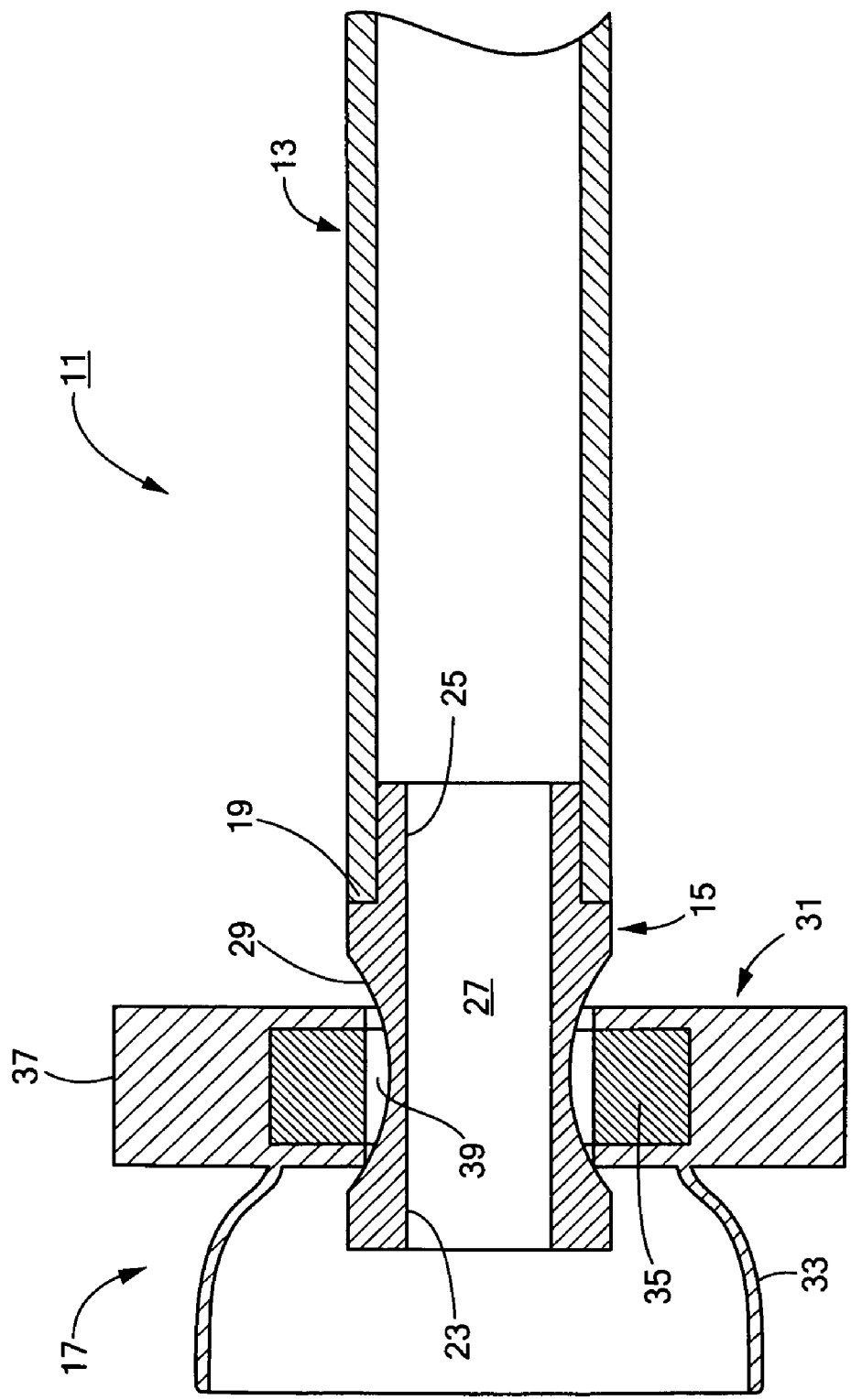
FIG. 3 is an enlarged longitudinal section view of the catheter assembly shown in FIG. 1.

Referring now to FIGS. 1 through 3, there are shown side, partially exploded perspective and enlarged longitudinal section views, respectively, of a first embodiment of a catheter assembly constructed according to the teachings of the present invention, said catheter assembly being represented generally by reference numeral 11.

Catheter assembly 11 includes a medical catheter 13, a fitting 15 and an internal bolster 17.

Catheter 13, which may be a conventional gastrostomy feeding tube, is an elongated, tubular member preferably made of a flexible, biocompatible material, such as a silicone rubber. Catheter 13 has a first end 19 and a second end 21. A series of ruler markings (not shown) are printed on catheter 13 and extend several inches from first end 19 in the direction of second end 21 to facilitate the cutting of catheter 13 to a desired length after catheter 13 has been implanted in a patient.

Fitting 15, which serves to couple bolster 17 to catheter 13, is an elongated, tubular member preferably made of a rigid, biocompatible material, such as a rigid polyethylene. Fitting 15 is shaped to include a first section 23 and a second section 25, first section 23 and second section 25 jointly defining a longitudinal bore 27 of uniform diameter. First section 23 has an outer diameter substantially equal to that of catheter 13, except for an intermediate waist portion 29 of narrowed outer diameter. Second section 25 of fitting 15 is securely disposed within first end 19 of catheter 13, with first end 19 of catheter 13 preferably being over-molded around second section 25 of fitting 15. Alternatively, instead of over-molding catheter 13 around second section 25 of fitting 15, one could securely retain second section 25 of fitting 15 within catheter 13 by a friction fit, by use of an appropriate adhesive or by other suitable means.

Internal bolster 17 includes a first section 31 and a second section 33. First section 31, which is appropriately dimensioned and constructed to internally anchor catheter 13 within a patient, is a generally annular member having an inner portion 35 and an outer portion 37, inner portion 35 and outer portion 37 jointly defining a central opening 39. Inner portion 35, which is preferably made of a rigid, biocompatible material, such as a rigid polyethylene, is coaxially mounted on waist portion 29 of fitting 15 by a snap-fit. Outer portion 37, which is preferably made of a flexible, biocompatible material, such as a polyurethane or a silicone rubber, is over-molded around inner portion 35.

Second section 33, whose purpose will be described below, is a generally bowl-shaped member whose narrower end is attached to outer portion 37 of first section 31. Second section 33 is preferably made of the same type of material as outer portion 37 of first section 31 and is preferably molded together with outer portion 37.

Figure 4A:
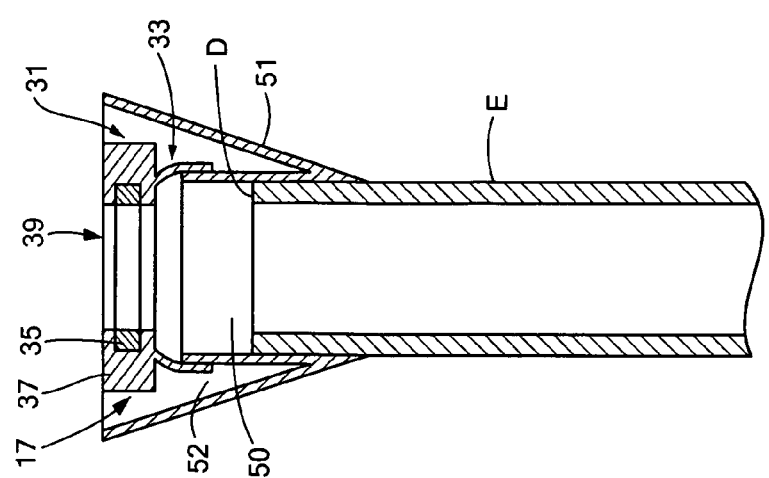
FIGS. 4(a) through (f) are fragmentary schematic views, partly in section, illustrating the manner in which the catheter assembly of FIG. 1 may be assembled and implanted in a patient in accordance with the teachings of the present invention.
Figure 4B:
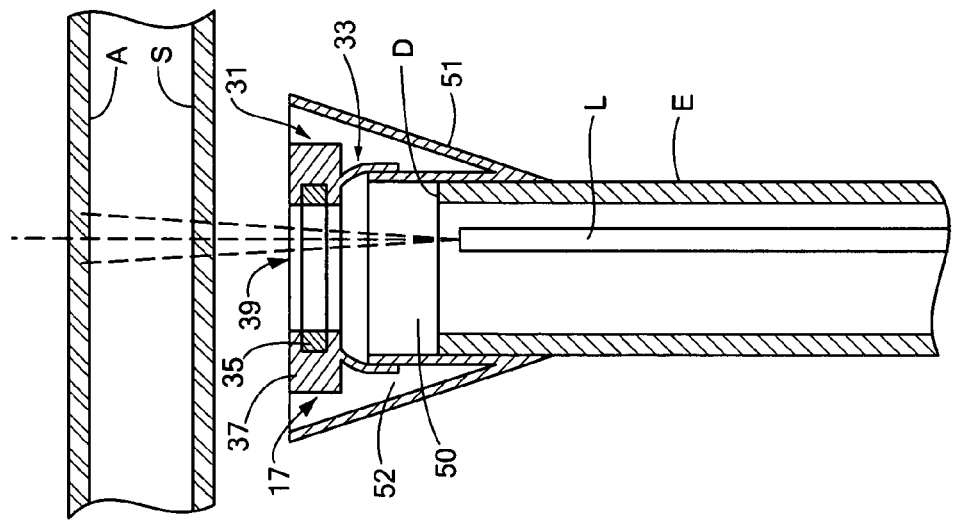

Referring now to FIGS. 4(a) through 4(f), there is schematically shown the manner in which catheter assembly 11 may be assembled and implanted in a patient. (For illustrative purposes, catheter assembly 11 is herein shown as an initial placement PEG device being implanted in the stomach of a patient; however, it is to be understood that catheter assembly 11 is not limited to being implanted in the stomach of a patient and may be installed at other locations within a patient where the delivery and/or drainage of fluids is desirable.) First, as seen in FIG. 4(a), prior to attending to the patient, the distal end D of an endoscope E is inserted into a first compartment 50 of a scope cap 51 and is retained therein by a friction-fit. In addition, bolster 17 is mounted within a second compartment 52 of scope cap 51 and is retained therein by a friction-fit between second section 33 and scope cap 51. For reasons to become apparent below, the friction-fit of endoscope E to scope cap 51 is sufficiently strong that scope cap 51 remains on endoscope E for the duration of the catheter implanting procedure. By contrast, the friction-fit of bolster 17 to scope cap 51 need only be strong enough to ensure the delivery of bolster 17 to fitting 15. Next, as seen in FIG. 4(b), distal end D of endoscope E is inserted transorally into the stomach of a patient, and an intense light source L disposed within endoscope E is used to transilluminate the stomach wall S and the abdominal wall A of the patient so as to indicate externally a desired incision site. Preferably, while the aforementioned transillumination process is conducted, a supply of gas is used to inflate the patient's stomach, thereby distending the stomach and facilitating the transillumination process.

Figure 4C:
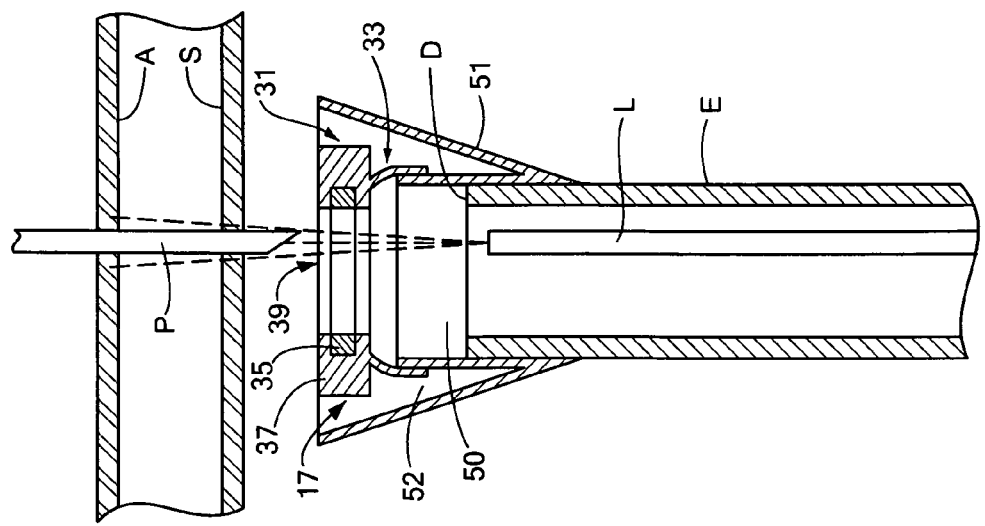
Figure 4D:
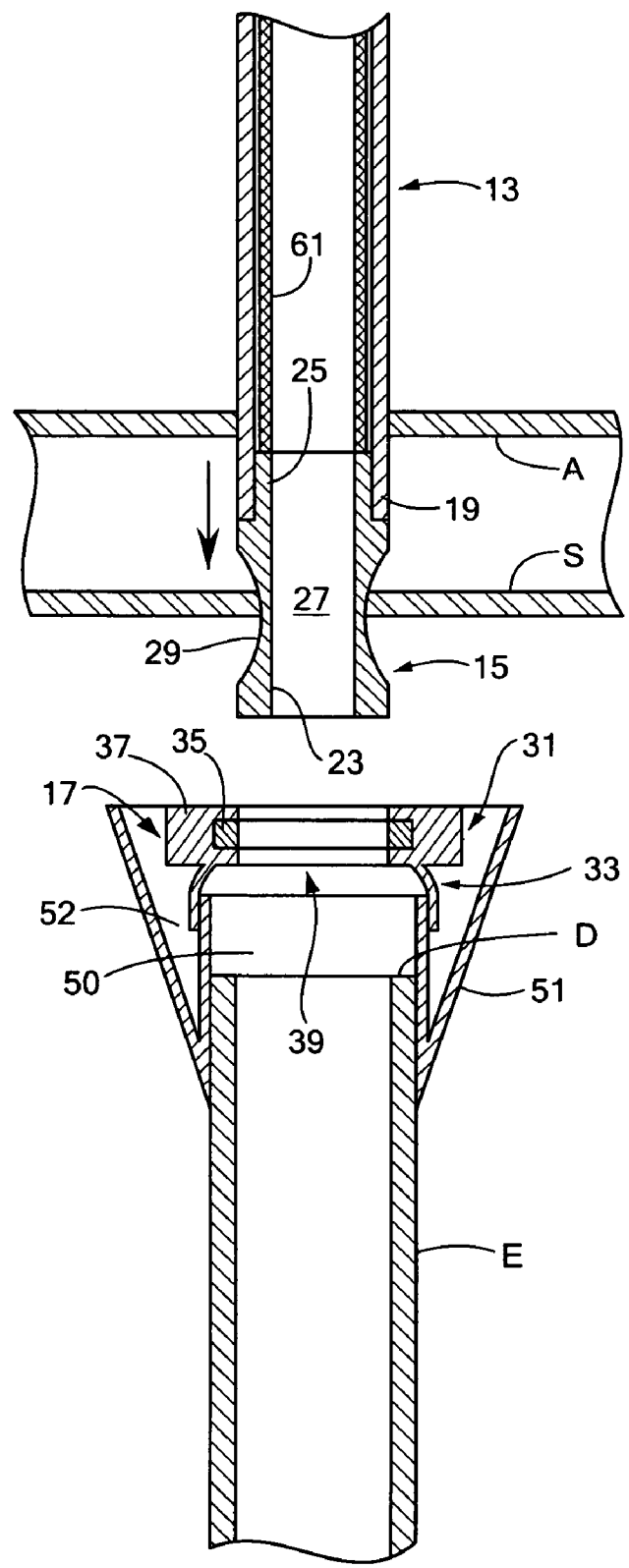
Figure 4E:
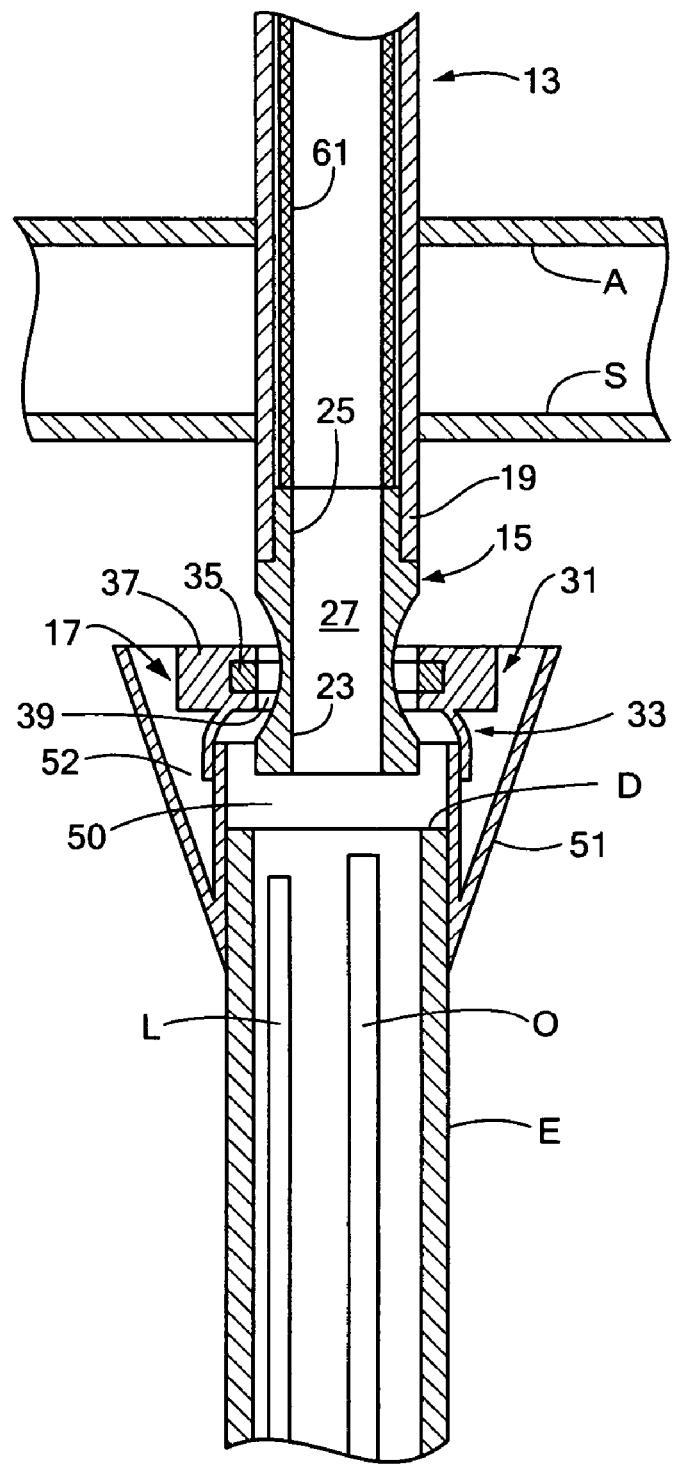
Figure 4F:
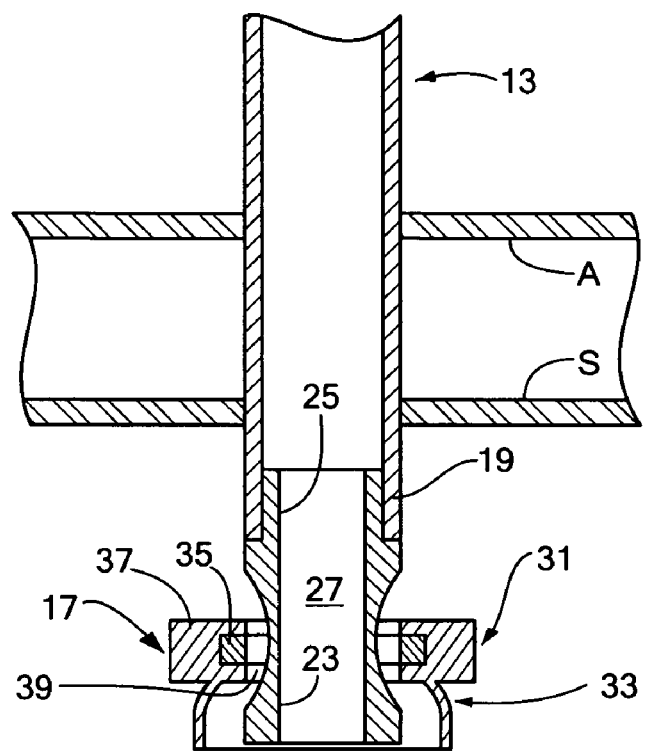
Figure 4F:
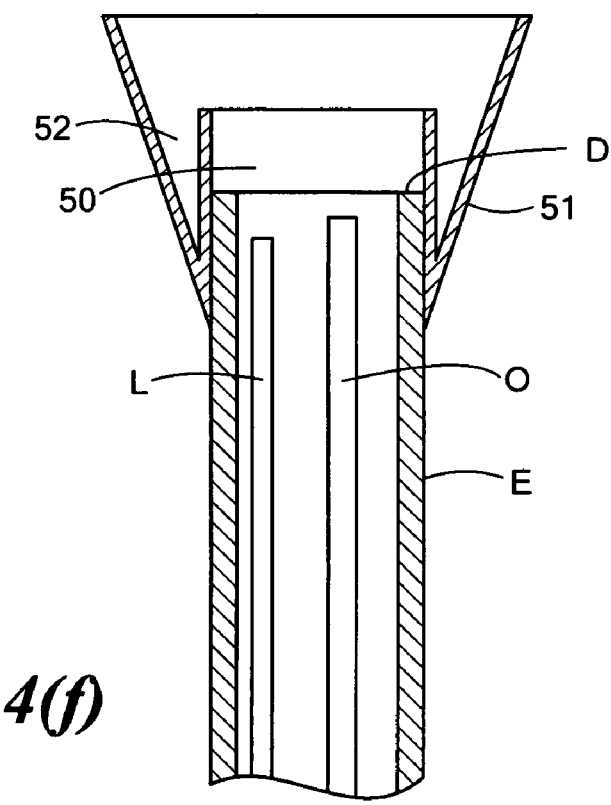

Next, as seen in FIG. 4(c), using a scalpel P, incisions are made in the abdominal wall A and in the stomach wall S of the patient at the desired incision site. Then, as seen in FIG. 4(d), fitting 15 and a portion of catheter 13 are inserted through the abdominal wall A and the stomach wall S at the incision site. Because catheter 13 possesses limited inherent stiffness and, therefore, may not be inserted easily through the incision site, a cannula 61 may be inserted into catheter 13 to provide stiffening support thereto, thereby facilitating its insertion. (It should be noted that, if cannula 61 were modified to include a sharpened end extending through fitting 15, cannula 61 could also be used, as in a direct PEG technique, to make the incisions in the abdominal and stomach walls of the patient, thereby obviating the need for a scalpel and a separate step to make such incisions.) Next, as seen in FIG. 4(e), while observing fitting 15 using observation optics O disposed within endoscope E, fitting 15 and bolster 17 are moved relative to one another until bolster 17 is inserted over fitting 15 and snap-fits thereon. Next, as seen in FIG. 4(f), cannula 61 is removed from catheter 13, and distal end D of endoscope E and scope cap 51 are drawn away from fitting 15. Because bolster 17 has previously been snap-fit onto fitting 15 in the manner described above, the drawing away of endoscope E and scope cap 51 from fitting 15 results in the removal of bolster 17 from scope cap 51. This leaves bolster 17 to internally anchor catheter 13 in the stomach of the patient, with the free end of catheter 13 extending out of the patient's abdomen. The implanted device may then be endoscopically checked for proper placement, cut to a desired length, and secured to an external bolster, Y-port and/or clamp in the conventional manner.

With catheter assembly 11 thus implanted in a patient, catheter assembly 11 is preferably able to withstand a pull force of about 14 pounds applied to free end 21 of catheter 13, without causing catheter 13 to separate from bolster 17.

The present invention provides a number of significant advantages over conventional catheter assemblies and methods for implanting the same in a patient's body. For example, with respect to conventional PEG devices of the type that are implanted using the above-described "push" and "pull" percutaneous endoscopic techniques, one advantage of the present invention is that the feeding tube is not passed through the oral cavity of the patient prior to being implanted in the stomach, but rather, is inserted directly into the stomach through the abdomen. This is advantageous because it is believed by many people that the passage of the feeding tube through the oral cavity increases the risk of infection to the incision site as bacteria present in the oral cavity are picked up by the feeding tube and carried to the incision site. By contrast, according to the present invention, only the internal bolster is passed through the oral cavity; however, because the internal bolster is not, itself, inserted into the incision and because the internal bolster is shielded, to a certain extent, from contact with bacteria by the scope cap, it is believed by the present inventors that the passage of the internal bolster through the oral cavity does not significantly increase the risk of infection to the incision site.

Moreover, the push and pull methods described above require that an endoscope be introduced into the patient twice—first to deliver the snared guidewire or suture through the patient's mouth to the clinician and then again to permit a visual inspection of the placement of the internal bolster in the patient's stomach after the PEG device has been implanted. Unfortunately, the second intubation of the endoscope is often very difficult and/or painful because of damage caused during the first placement or due to the patient's anatomy or disease state. This problem is avoided in the present technique as the endoscope need only be inserted once into the patient.

The present invention is also believed to have advantages over conventional direct percutaneous techniques of the type described above wherein not only the feeding tube but also the internal bolster is inserted directly through the abdomen. In the case of such direct percutaneous techniques, the insertion of the internal bolster through the abdomen typically requires an incision to be made that is sufficiently large to accommodate the insertion of the internal bolster therethrough or requires the use of an internal bolster that may be compressed while passing through the abdomen and then expanded once properly positioned in the stomach. By contrast, because the internal bolster of the present assembly is not passed through the abdomen, one advantage of the present invention is that the incision in the abdominal and stomach walls may be kept as small as possible. In addition, because the internal bolster is not passed through the abdomen, one need not use a reversibly expandable bolster, such bolsters tending to experience a high failure rate; instead, one may use a more rigid or shape-retaining internal bolster.

Figure 5A:
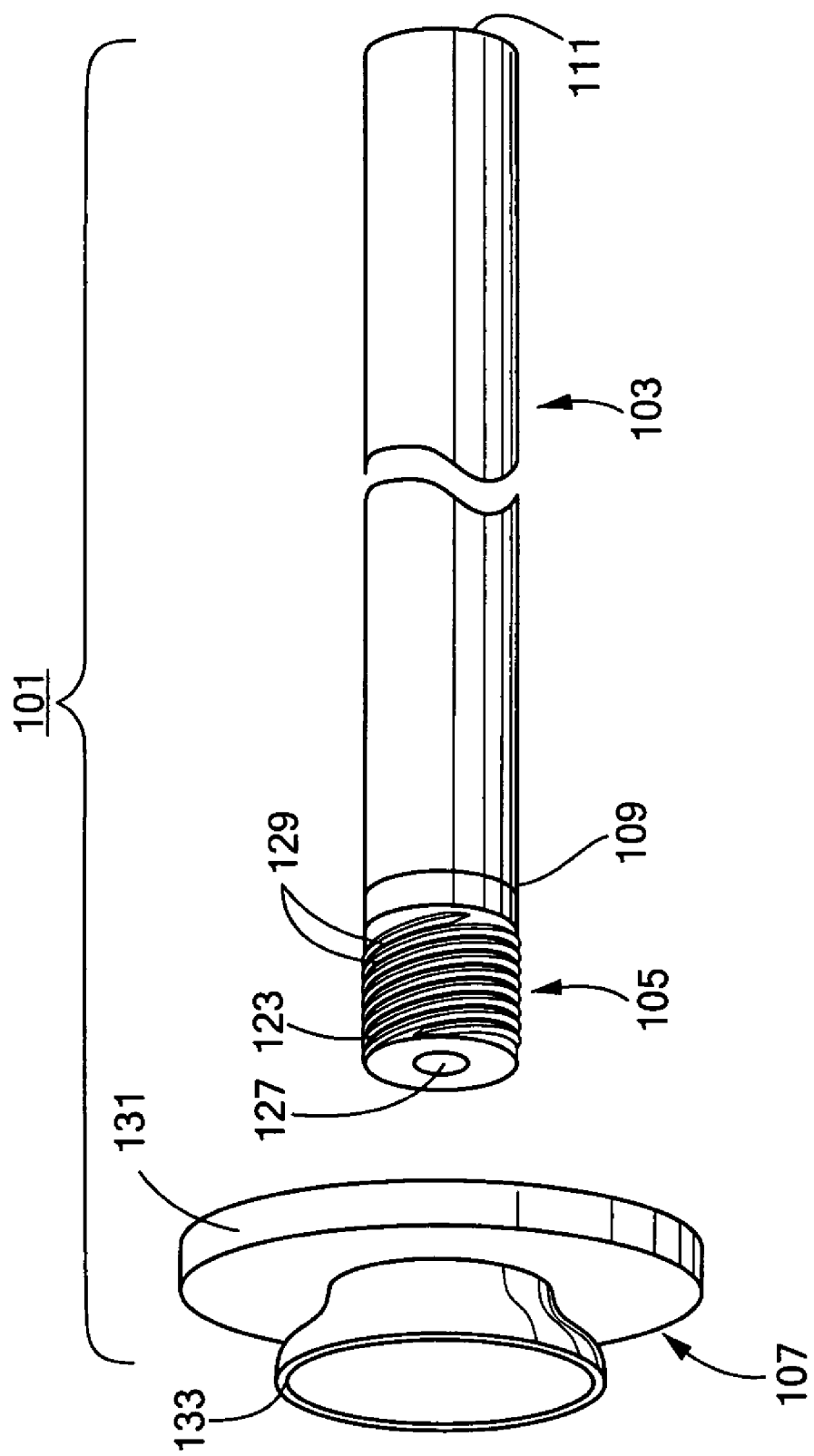
FIGS. 5(a) and 5(b) are partially exploded, perspective and longitudinal section views, respectively, of a second embodiment of a catheter assembly constructed according to the teachings of the present invention.
Figure 5B:
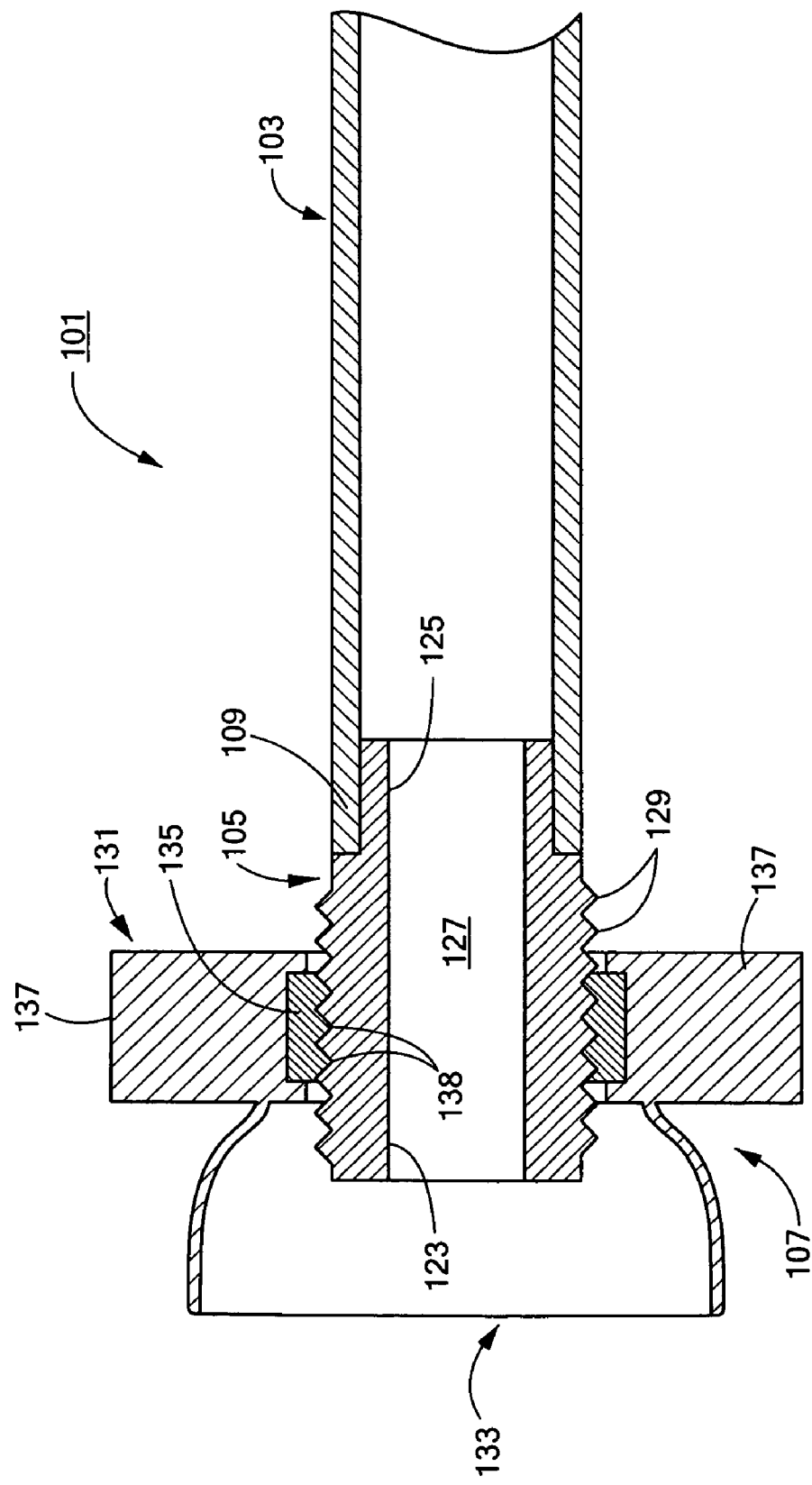

Referring now to FIGS. 5(a) and 5(b), there are shown partially exploded perspective and longitudinal section views, respectively, of a second embodiment of a catheter assembly constructed according to the teachings of the present invention, said catheter assembly being represented generally by reference numeral 101.

Catheter assembly 101 includes a medical catheter 103, a fitting 105 and an internal bolster 107.

Catheter 103, which may be identical to catheter 13 of catheter assembly 11, is an elongated, tubular member having a first end 109 and a second end 111.

Fitting 105 is an elongated, tubular member preferably made of a rigid, biocompatible material, such as a rigid polyethylene. Fitting 105 is shaped to include a first section 123 and a second section 125, first section 123 and second section 125 jointly defining a longitudinal bore 127 of uniform diameter. First section 123 has an outer diameter substantially equal to that of catheter 103 and is shaped to include an external thread 129. Second section 125 of fitting 105 is securely disposed within first end 109 of catheter 103, with first end of catheter 103 preferably being over-molded around second section 125 of fitting 105. Alternatively, instead of over-molding catheter 103 around second section 125 of fitting 105, one could securely retain second section 125 of fitting 105 within catheter 103 by a friction fit, by use of an appropriate adhesive or by other suitable means.

Internal bolster 107 includes a first section 131 and a second section 133. First section 131, which is appropriately dimensioned and constructed to internally anchor catheter 103 within a patient, is a generally annular member having an inner portion 135 and an outer portion 137, inner portion 135 defining a central opening. Inner portion 135, which is preferably made of a rigid, biocompatible material, such as a rigid polyethylene, has an internal thread 138 that engages thread 129 of fitting 105 by a screw-fit. Outer portion 137, which is preferably made of a flexible, biocompatible material, such as a polyurethane or silicone rubber, is over-molded around inner portion 135.

Second section 133, which is similar in structure and function to second section 33 of assembly 11, is preferably made of the same type of material as outer portion 137 of first section 131 and is preferably molded together with outer portion 137.

Assembly 101 is used in much the same manner as assembly 11, the principal difference between the two assemblies being that, with assembly 101, bolster 107 is mounted on fitting 105 by a screw-fit, as opposed to a snap-fit. The threading together of bolster 107 and fitting 105 for such a screw-fit is preferably accomplished by keeping bolster 107 stationary while rotating fitting 105 and catheter 103 about their longitudinal axes (e.g., with the assistance of a cannula or like device inserted into catheter 103).

Figure 6A:
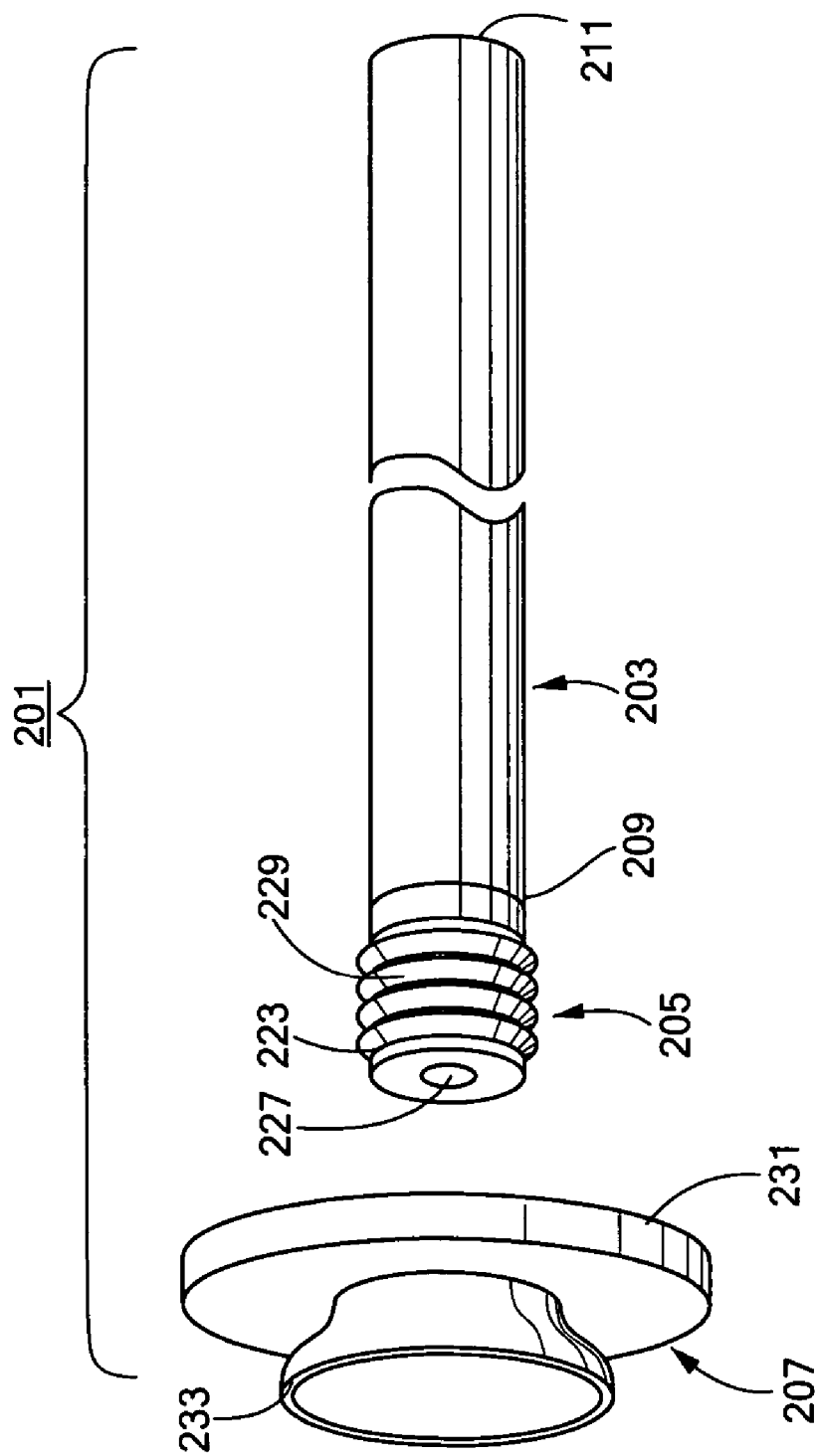
FIGS. 6(a) and 6(b) are partially exploded, perspective and longitudinal section views, respectively, of a third embodiment of a catheter assembly constructed according to the teachings of the present invention.
Figure 6B:
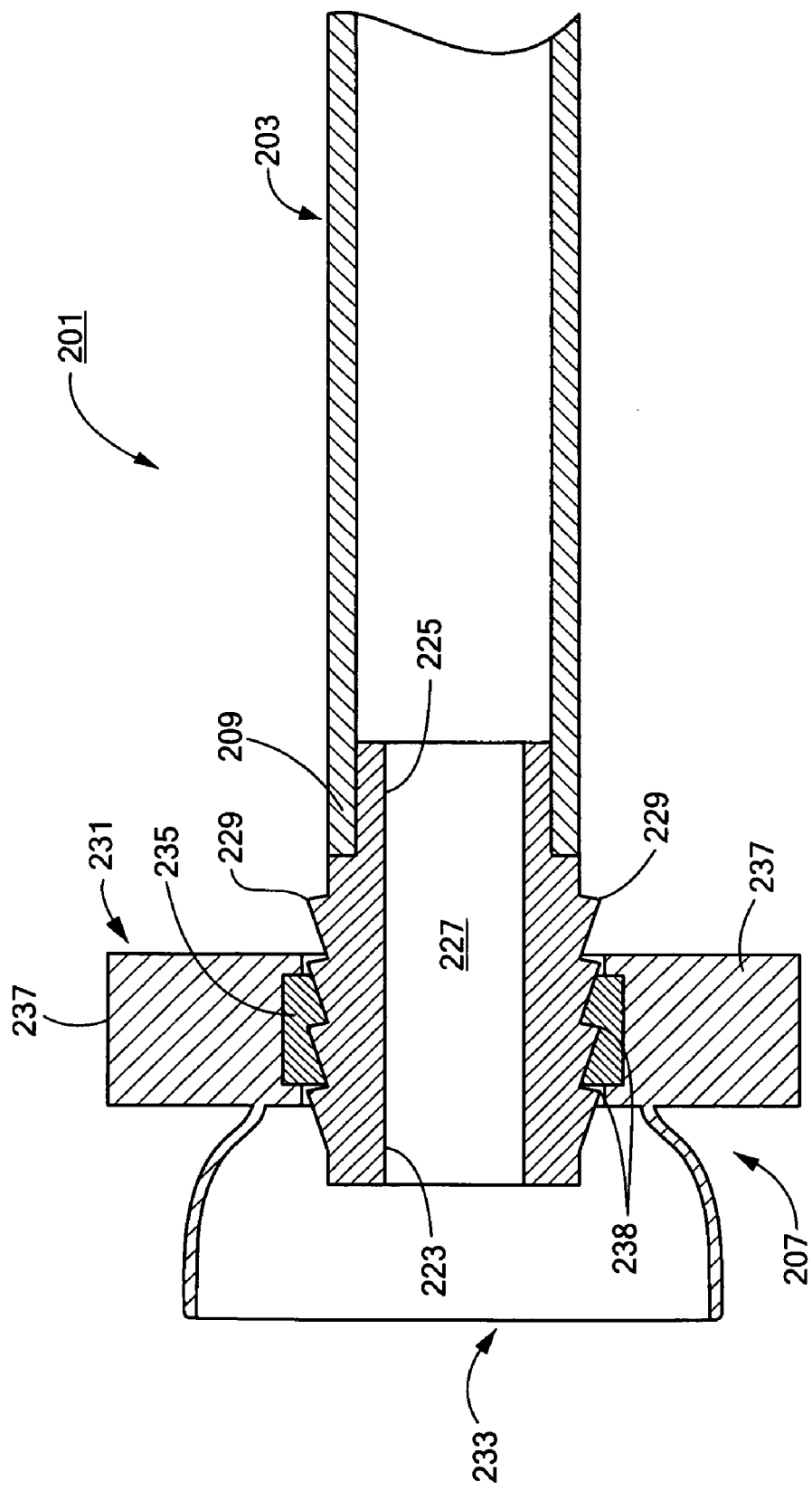

Referring now to FIGS. 6(a) and 6(b), there are shown partially exploded perspective and longitudinal section views, respectively, of a third embodiment of a catheter assembly constructed according to the teachings of the present invention, said catheter assembly being represented generally by reference numeral 201.

Catheter assembly 201 includes a medical catheter 203, a fitting 205 and an internal bolster 207.

Catheter 203, which may be identical to catheter 13 of catheter assembly 11, is an elongated, tubular member having a first end 209 and a second end 211.

Fitting 205 is an elongated, tubular member preferably made of a rigid, biocompatible material, such as a rigid polyethylene. Fitting 205 is shaped to include a first section 223 and a second section 225, first section 223 and second section 225 jointly defining a longitudinal bore 227 of uniform diameter. First section 223 has an outer diameter substantially equal to that of catheter 203 and is shaped to include a plurality of external barbs 229. Second section 225 of fitting 205 is securely disposed within first end 209 of catheter 203, with first end of catheter 203 preferably being over-molded around second section 225 of fitting 205. Alternatively, instead of over-molding catheter 203 around second section 225 of fitting 205, one could securely retain second section 225 of fitting 205 within catheter 203 by a friction fit, by use of an appropriate adhesive or by other suitable means.

Internal bolster 207 includes a first section 231 and a second section 233. First section 231, which is appropriately dimensioned and constructed to internally anchor catheter 203 within a patient, is a generally annular member having an inner portion 235 and an outer portion 237, inner portion 235 defining a central opening. Inner portion 235, which is preferably made of a rigid, biocompatible material, such as a rigid polyethylene, has a plurality of internal barbs 238 that engage external barbs 229 of fitting 205 by a snap-fit. Outer portion 237, which is preferably made of a flexible, biocompatible material, such as a polyurethane or a silicone rubber, is over-molded around inner portion 235.

Second section 233, which is similar in structure and function to second section 33 of assembly 11, is preferably made of the same type of material as outer portion 237 of first section 231 and is preferably molded together with outer portion 237.

Assembly 201 is used in much the same manner as assembly 11, the principal difference between the two assemblies being that, with assembly 201, bolster 207 is mounted on fitting 205 by inserting first section 223 of fitting 205 into central opening 239 of bolster 207 until barbs 238 and 229 snap-fit together.

Figure 7A:
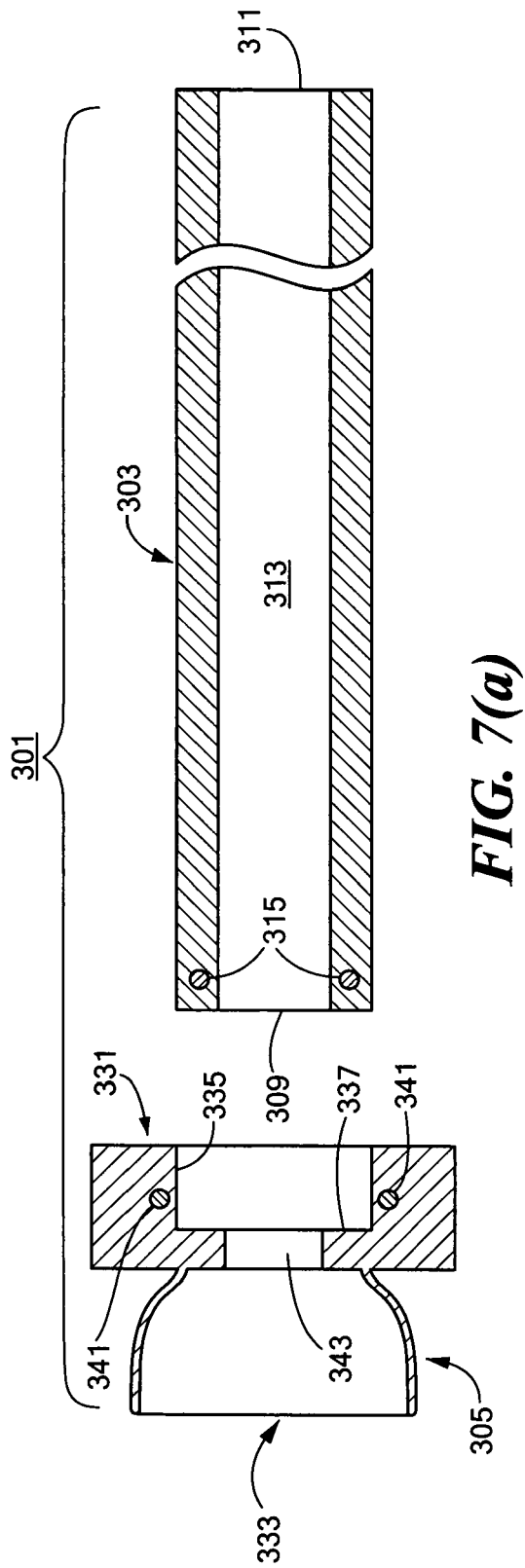
FIGS. 7(a) and 7(b) are partially exploded longitudinal section and longitudinal section views, respectively, of a fourth embodiment of a catheter assembly constructed according to the teachings of the present invention.
Figure 7B:
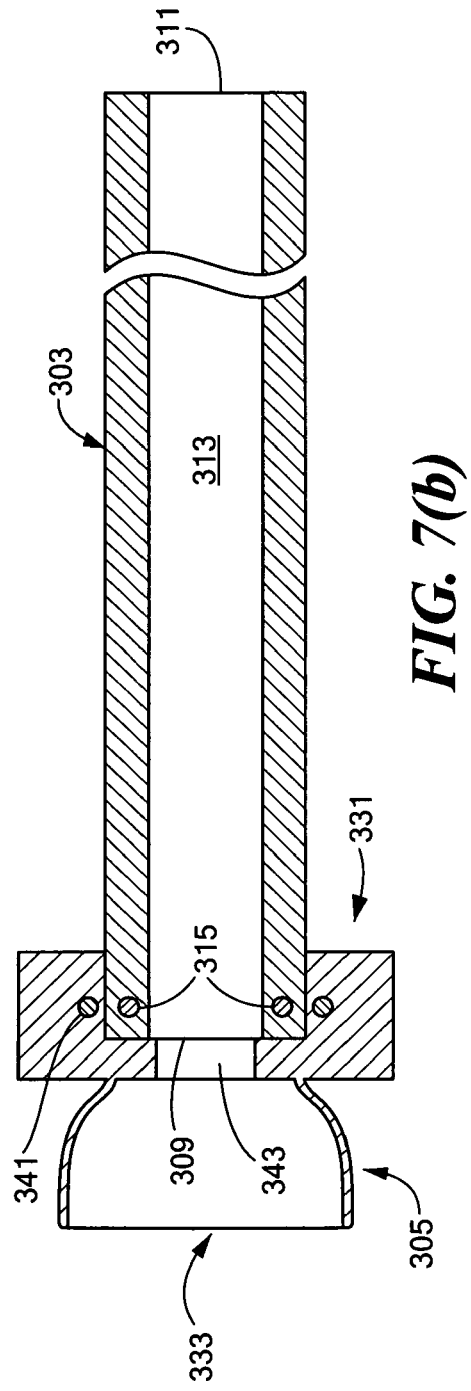

Referring now to FIGS. 7(a) and 7(b), there are shown partially exploded longitudinal section and longitudinal section views, respectively, of a fourth embodiment of a catheter assembly constructed according to the teachings of the present invention, said catheter assembly being represented generally by reference numeral 301.

Assembly 301 comprises a catheter 303 and an internal bolster 305.

Catheter 303 is a flexible, biocompatible, tubular member, preferably made of a silicone rubber, catheter 303 having a first end 309, a second end 311 and a longitudinal bore 313. A plurality of magnetic spheres 315 are embedded within catheter 303 at first end 309, spheres 315 being peripherally dispersed around bore 313.

Bolster 305 includes a first section 331 and a second section 333. First section 331, which is appropriately dimensioned and constructed to internally anchor catheter 303 within a patient, is a flexible, biocompatible member, preferably made of a polyurethane or a silicone rubber, first section 331 being shaped to include a circular side wall 335, an end wall 337 and an open receiving end. First section 331 snugly receives first end 309 of catheter 303 against side wall 335 and end wall 337. A plurality of magnetic spheres 341 are embedded within side wall 335, magnetic spheres 341 being appropriately positioned and oppositely magnetized relative to magnetic spheres 315 to promote the retention of catheter 303 within first section 331. A central opening 343 is provided in end wall 337, opening 343 being aligned with bore 313 of catheter 303 to permit fluid communication therebetween.

Second section 333, which is similar in structure and function to second section 33 of assembly 11, is preferably molded together with first section 331.

Assembly 301 is used in much the same manner as assembly 11, the principal difference between the two assemblies being that, with assembly 301, bolster 307 is mounted on fitting 305 by inserting first end 309 of catheter 303 through the receiving end of first section 331 until magnetic spheres 315 and magnetic spheres 341 are drawn together by magnetic attraction.

In another embodiment of the invention (not shown), bolster 17 is modified so that inner portion 35 is constructed of a shape memory alloy. In this manner, after the modified bolster is inserted around fitting 15, the bolster is expanded to a size that fits tightly around fitting 15. Expansion of the bolster may be effected by heating, either by an external source or by the patient's own body temperature.

In still another embodiment of the invention (not shown), the bolster may be formed as two semi-annular members that are coupled to one another around the fitting.

Other bolster attachment or attachment enhancement means may include adhesives, velcro, a pawl and ratchet system, barbs, solvents, key and lock arrangements or an application of energy, such as heat or light, to activate an adhesive, to activate an attachment means or to melt components.

With respect to one or more of the catheter assemblies described above, although it is presently intended that the bolster remain connected to the catheter following assembly, it should be understood that, if desired, it is possible to disconnect the bolster from the catheter and, thereafter, to reconnect the bolster to the catheter.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A catheter assembly comprising:
   (a) a catheter, said catheter having a distal end and a proximal end, said proximal end adapted to extend through the abdominal wall out of a patient's body;
   (b) a tubular fitting, said tubular fitting having a proximal portion and a distal portion, said proximal portion being secured to said distal end of said catheter, said distal portion comprising a waist portion of decreased outer diameter;

(c) a bolster for anchoring the catheter within a cavity of the patient, said bolster having an annular portion with a first central opening wherein the waist portion of the tubular fitting is adapted to be received within the first central opening of the bolster by a snap-fit; and an endoscope cap having a first compartment and a second compartment, wherein a distal end of an endoscope is adapted to be received within the first compartment, and said bolster is removably received within the second compartment.

2. The catheter assembly as claimed in claim 1 wherein said first end of said catheter is over-molded around a portion of said tubular fitting.

3. The catheter assembly as claimed in claim 1 wherein said bolster is an internal bolster.

4. A catheter assembly comprising:
(a) a catheter, said catheter having a first end and a second end, said second end adapted to extend out of a patient's body;
(b) a tubular fitting on the first end of said catheter;
(c) an internal bolster, said internal bolster having an annular portion with a first central opening, said internal bolster being reversibly detachably coupled to said first end of said catheter by the tubular fitting; and
(d) an endoscope cap having a first compartment and a second compartment, wherein a distal end of an endoscope is adapted to be received within the first compartment, and said bolster is removably received within the second compartment.

5. The catheter assembly as claimed in claim 4 wherein said internal bolster is reversibly detachably mounted on said tubular fitting.

6. The catheter assembly as claimed in claim 5 wherein said first end of said catheter is over-molded around a portion of said tubular fitting.

7. The catheter assembly as claimed in claim 5 wherein said tubular fitting includes a waist portion of decreased outer diameter and wherein said first central opening of the internal bolster is appropriately sized for a snap-fit with said waist portion, said tubular fitting being inserted into said first central opening and secured thereto by a snap-fit.

8. A catheter assembly kit comprising:
(a) a catheter, said catheter having a first end and a second end, said second end adapted to extend out of a patient's body;
(b) a bolster, said bolster having an annular portion with a first central opening;
(c) means for physically coupling said bolster to said first end of said catheter; and
(d) an endoscope cap having a first compartment and a second compartment, wherein a distal end of an endoscope is adapted to be received within the first compartment, and said bolster is removably received within the second compartment.

9. The catheter assembly kit as claimed in claim 8 wherein said coupling means comprises a tubular fitting coupled to said first end of said catheter, said bolster being adapted to be secured around said tubular fitting.

10. The catheter assembly kit as claimed in claim 9 wherein said tubular fitting includes a waist portion of decreased outer diameter and wherein said first central opening of the bolster is appropriately sized so that said bolster may be inserted over said tubular fitting and secured to said waist portion by a snap-fit.

11. The catheter assembly kit as claimed in claim 9 wherein said catheter is over-molded around a portion of said tubular fitting.

12. The catheter assembly kit as claimed in claim 8 wherein said catheter is a feeding tube adapted to extend through the abdominal wall.

13. The catheter assembly kit as claimed in claim 12 wherein said feeding tube is a gastrostomy feeding tube adapted to extend through the abdominal wall.

14. The catheter assembly kit as claimed in claim 8 wherein said bolster comprises mounting means adapted for attachment to the endoscope cap.

15. The catheter assembly kit as claimed in claim 8 wherein said bolster is an internal bolster.

16. The catheter assembly as claimed in claim 1 wherein the annular portion of the bolster has an inner portion and an outer portion, said inner portion comprising a first material and said outer portion comprising a second material, wherein said first material and said second material are different.

17. The catheter assembly as claimed in claim 16 wherein said first material comprises a rigid biocompatible material and said second material comprises a flexible biocompatible material.

18. The catheter assembly as claimed in claim 16 wherein said first material is more rigid than said second material.

19. The catheter assembly as claimed in claim 1 wherein the tubular fitting comprises a bore of uniform diameter.

20. The catheter assembly as claimed in claim 1 wherein said distal portion of the tubular fitting, except for the waist portion, has an outer diameter equal to an outer diameter of the catheter.

21. The catheter assembly as claimed in claim 1 wherein the proximal portion of the tubular fitting is received within the distal end of the catheter and secured therein by a friction fit and/or by an adhesive.

22. The catheter assembly as claimed in claim 1 wherein said bolster further comprises a bowl-shaped member with a second central opening.

23. The catheter assembly as claimed in claim 22 wherein said tubular fitting has a distal end extending into the second central opening.

24. The catheter assembly as claimed in claim 4 wherein said internal bolster further comprises a bowl-shaped member with a second central opening.

25. The catheter assembly as claimed in claim 8 wherein said bolster further comprises a bowl-shaped member with a second central opening.

26. The catheter assembly of claim 1, wherein said bolster further comprises a bowl-shaped portion with an open distal end, wherein said open distal end of the bowl-shaped portion has an outer diameter such that it is removably attached to the scope cap.

27. The catheter assembly of claim 1, wherein the endoscope cap has a first inner wall surrounding a central opening and a second outer wall surrounding the inner wall.

28. The catheter assembly of claim 27, wherein the inner wall has a cylindrical shape and the proximal end thereof forms the first compartment.

29. The catheter assembly of claim 28, wherein the inner wall and the outer wall are joined at a proximal end of the endoscope cap.

30. The catheter assembly of claim 28, wherein the outer wall has a conical shape and the distal end thereof forms the second compartment.

31. The catheter assembly of claim 30, wherein a proximal end of the outer wall has a smaller diameter than a distal end of the outer wall.

* * * * *